United States Patent
Thompson

(10) Patent No.: US 10,765,707 B2
(45) Date of Patent: Sep. 8, 2020

(54) HONEY-BASED GEL COMPOSITION

(71) Applicant: Derma Sciences, Inc., Princeton, NJ (US)

(72) Inventor: Fatma Bilge Thompson, Pyes Pa (NZ)

(73) Assignee: Derma Sciences, Inc., Princeton, NJ (US)

(*) Notice: Subject to any disclaimer, the term of this patent is extended or adjusted under 35 U.S.C. 154(b) by 757 days.

(21) Appl. No.: 14/942,721

(22) Filed: Nov. 16, 2015

(65) Prior Publication Data

US 2016/0067288 A1 Mar. 10, 2016
US 2020/0215122 A9 Jul. 9, 2020

Related U.S. Application Data

(63) Continuation of application No. 13/637,261, filed as application No. PCT/NZ2011/000046 on Apr. 7, 2011, now abandoned.

(30) Foreign Application Priority Data

Apr. 7, 2010 (NZ) ...................................... 584463

(51) Int. Cl.

| | |
|---|---|
| A61K 35/644 | (2015.01) |
| A61L 26/00 | (2006.01) |
| A61K 9/00 | (2006.01) |
| A61K 9/06 | (2006.01) |
| A61K 31/23 | (2006.01) |
| A61K 31/7028 | (2006.01) |

(52) U.S. Cl.
CPC .......... *A61K 35/644* (2013.01); *A61K 9/0014* (2013.01); *A61K 9/06* (2013.01); *A61K 31/23* (2013.01); *A61K 31/7028* (2013.01); *A61L 26/0057* (2013.01)

(58) Field of Classification Search
None
See application file for complete search history.

(56) References Cited

U.S. PATENT DOCUMENTS

| | | | |
|---|---|---|---|
| 5,965,145 | A | 10/1999 | Marion et al. |
| 6,171,604 | B1 | 1/2001 | Mousa |
| 6,482,442 | B1 | 11/2002 | Dado |
| 2004/0121020 | A1* | 6/2004 | Moloney .................. A61L 15/34 424/539 |

FOREIGN PATENT DOCUMENTS

| | | |
|---|---|---|
| AU | 2003234758 | 3/2004 |
| GB | 2391809 A | 2/2004 |
| WO | WO-2007/137369 A1 | 12/2007 |

OTHER PUBLICATIONS

Ash et al. "caprylyl/capryl glucoside" from Handbook of Green Chemicals. 2004. p. 659. (Year: 2004).*
BusinessWire. Derma Sciences Announces Launch of MediHoney (TM) Wound Care Dressings. Oct. 17, 2007. Retrieved from the internet on: Dec. 4, 2018. Retrieved from: <URL: https://www.businesswire.conn/news/home/20071017005158/en/Derma-Sciences-Announces-Launch-MEDIHONEY-TM-Wound>. (Year: 2007).*
Simon et al. Advance Access Publication Jan. 7, 2008 eCAM 2009;6(2)165-173. (Year: 2008).*
Medihoney Antibacterial Wound Gel 50g: Amazon.co.uk: Health & Personal Care. Retrieved from the Internet on: Dec. 4, 2018. Retrieved from: <URL: https://www.amazon.co.uk/Medihoney-Antibacterial-Wound-Gel-50g/dp/B00GTDHAAA>. (Year: 2018).*
Ash et al. Caprylylic/caprylic glucoside in "Handbook of Green Chemicals." Synapse Information Resources, Inc.: NY. 2004. p. 659.
Notification of Transmittal of the International Search Report and the Written Opinion of the International Searching Authority, PCT/NZ2011/000049, dated Jun. 8, 2011.
Supplementary European Search Report issued for European Patent Application No. 11766211.4 dated Nov. 8, 2013. 4 pages.
Food and Drug Administration, Department of Health & Human Services, Letter providing marketing approval for the *Derma Sciences API-MED™ Active Manuka Honey Absorbent Dressing*, Jul. 12, 2007, 3 pages.
Food and Drug Administration 510(k) Summary for *Derma Sciences Medihoney Primary Dressings with Active Manuka Honey*, Nov. 7, 2007, 6 pages.

* cited by examiner

*Primary Examiner* — Amy L Clark
(74) *Attorney, Agent, or Firm* — Morrison & Foerster LLP

(57) ABSTRACT

A honey based composition is described. The composition includes a mixture of honey, a short chain fatty alcohol and a fatty ester or wax. The composition has applications for use in wound dressings and in one embodiment may be a gel. The composition has a higher than expected storage stability, remaining stable for many weeks when held at elevated temperatures and retains all of the other desirable characteristics including anti-microbial activity.

20 Claims, No Drawings

HONEY-BASED GEL COMPOSITION

RELATED APPLICATIONS

This application is a continuation of U.S. application Ser. No. 13/637,261, now abandoned, which is a U.S. National Stage Entry of International Application No. PCT/NZ2011/000049, filed on Apr. 7, 2011, which claims priority from NZ584463 dated Apr. 7, 2010, the contents of which are incorporated herein by reference.

TECHNICAL FIELD

The present application relates to a gel composition. More specifically, the application relates to a storage stable and natural based composition containing honey that has a gel structure and, on application to a wound, forms a skin over the wound.

BACKGROUND ART

Honey used in wound dressings has been extensively discussed and taught in the art.

One of the difficulties of honey for use in wound dressing applications is that honey is a naturally sticky substance that if applied to a wound can be difficult to apply and runny. Solutions have been proposed in the art to overcome this drawback of honey and yet still maintain the honey efficacy in wound treatment.

One example is the use of alginate gums mixed with the honey to form gels. Another alternative is that described in U.S. Published Application No. 2010/0233283. This composition is useful in that the honey composition is a gel paste or ointment that can be easily packaged in a tube or other pliable container. The gel can easily be squeezed out of the tube and applied to a wound. The gel described in U.S. Published Application No. 2010/0233283 forms a skin over the wound, keeps its shape when applied to a wound (i.e. does not melt or run), and is easier to apply than pure honey. Further, the composition still retains sufficient honey to provide the desired honey antibacterial and wound healing effects. A drawback of the composition described in U.S. Published Application No. 2010/0233283 is that the composition when stored in the container over time can separate, particularly at temperatures over 30° C. This is undesirable as separation reduces efficacy and aesthetic characteristics of the gel.

Natural based products may also be desirable in many applications, sometimes for improved efficacy and often to aid in marketing the products as being natural based and therefore able to be used in a variety nutraceutical applications. A further drawback of the composition described in U.S. Published Application No. 2010/0233283 is that it uses a non-natural ingredient being an ethoxylated oil or PEG60.

It should be appreciated from the above that it would be useful to have a honey based wound dressing gel that was both shelf stable and utilised natural based ingredients. It is an object of the present application to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Further aspects and advantages of the gel composition described herein will become apparent from the ensuing description that is given by way of example only.

SUMMARY

The application broadly relates to a composition containing honey for use in wound dressings. The composition has a gel consistency that, on application to a wound forms skin over the wound. The composition is shelf stable and uses naturally produced products.

In some embodiments, there is provided a composition for treating a patient wherein the composition comprises:
    a. at least 50% wt honey or a honey derivative;
    b. 2-15% wt of a naturally derived short chain fatty alcohol with non-ionic surfactant properties;
    c. to 50% wt of a naturally derived fatty ester, a wax and wax-like compounds or mixtures thereof having a set point of 45° C. or less,
wherein the composition has been subjected to a sterilisation effective dosage of radiation and is storage stable for a time period of at least 24 hours at 40° C.

In some embodiments, there is provided a gel composition consisting of:
    a. 70-90% wt honey
    b. 2-15% wt myristyl myristate
    c. 2-10% wt caprylyl capryl glucoside.

The compositions have been found to have a far higher level of stability than existing art compositions. In some embodiments the applicant has noted a stability of over 5 weeks at 40° C. or at least 9 weeks when stored at 30° C., well beyond that of similar products that became unstable and separated after only 12 hours. A further advantage is that the compositions are naturally derived and do not use synthetically derived ingredients.

The compositions have applications as a wound gel stored in a tube and applied to the wound by dispensing the gel from the tube and then applying the gel to the wound surface. The composition acts to block egress of debris from outside the wound into the wound and, due to the antimicrobial and healing effects of honey, acts to prevent infection and assist wound healing. Since the honey levels in the composition can be kept high, the efficacy due the honey is retained. Conversely, the other ingredients used avoid other difficulties associated with using honey such as being difficult to apply due to it's stickiness and the fact that body temperature causes the honey to run or flow from the wound.

A further advantage of the above composition is that it may be irradiated using standard conditions with no loss in stability of other characteristics including efficacy. The art teaches about the difficulties of irradiation and how irradiation can reduce the efficacy, stability and physical properties of honey based compositions. Irradiation is however essential and an accepted form of sterilising honey based compositions used in wound healing. In the applicant's experience, irradiation of the honey based composition described herein does not alter the characteristics of the composition including stability.

DETAILED DESCRIPTION

As noted above, the application broadly relates to a composition containing honey for use in wound dressings. The composition has a gel consistency that, on application to a wound forms skin over the wound. The composition is shelf stable and uses naturally produced products.

For the purposes of this specification, the term 'surfactant' refers to a compound that is a wetting agent that reduces the surface tension of a liquid. Surfactants reduce the interfacial tension between oil and water by adsorbing at the liquid-liquid interface.

The term 'gel' refers to a fluidity that lies between a liquid and solid and may incorporate a degree of viscoelasticity.

The term 'stable' refers to the composition remaining in suspension and not undergoing physical, chemical, microbial growth change, or any loss in antibacterial action when stored for a period of time.

The terms 'UMF' and 'non-peroxide activity' refer to the activity of honey not directly attributable to the antimicrobial effects of honey conferred from the normal honey pH and osmolarity, for example that observed and measured in a naturally derived clover honey.

The term 'honey or honey derivative' refers to naturally derived honey or mixtures of honey but may also include honey analogues or derivatives such as sugar syrup solutions.

The term 'honey analogue' refers to a sugar syrup solution approximating that of honey e.g. including glucose, fructose, water and either hydrogen peroxide and/or one or more hydrogen peroxide precursors.

The term 'glucoside' in this specification may be used interchangeably with the term 'glycoside'.

The term 'sterilisation effective dosage of radiation' refers to a dose of radiation being at least 1 kGy or ideally 10 kGy or higher.

The term 'natural based' refers to compounds obtained from nature or one or more synthesised versions of compounds found in nature. Ideally, the compound or compounds used meet the Natural Products Association (NP) guidelines i.e. they are derived from renewable sources in nature' they do not use petroleum compounds, they meet generally recognised as safe or GRAS standard as set by the USA FDA and they are manufactured based on NPA approved processes.

In some embodiments, a composition is provided for treating a patient wherein the composition comprises:
 a. at least 50% wt honey or a honey derivative;
 b. 2-15% wt of a naturally derived short chain fatty alcohol with non-ionic surfactant properties;
 c. 1 to 50% wt of a naturally derived fatty ester, a wax and wax-like compounds or mixtures thereof having a set point of 45° C. or less,
 wherein the composition has been subjected to a sterilisation effective dosage of radiation and is storage stable for a time period of at least 24 hours at 40° C.

The composition has an unexpected and improved stability over the art. In some embodiments, the composition is stable for at least 8 days when stored at 40° C. In some embodiments, the composition is stable for at least 21 days when stored at 40° C. In some embodiments, the composition is stable for at least 9 weeks when stored at 30° C. In in some embodiments, the composition is stable for at least 15 weeks at 30° C. The anticipated stability when stored at typical ambient conditions is likely to be at least 3 years based on accelerated trials completed by the applicant. This degree of stability goes well beyond that observed by the applicants for equivalent compositions containing honey, particularly those that have a gel viscosity. For example, in the applicant's experience, the closest similar composition becomes unstable and phase separates after only 12 hours when stored at 40° C.

The composition is a gel. Gels are a useful consistency for application to wounds as the gel can easily by packaged, dispersed form the packaging and applied to almost any shaped wound. In some embodiments, the composition may have a viscosity of approximately $50 \times 10^3$ to $600 \times 10^3$ cPs at 25° C. In some embodiments, the viscosity may be $100 \times 10^3$ to $500 \times 10^3$ cPs at 25° C. In some embodiments, the viscosity may be $300 \times 10^3$ to $400 \times 10^3$ cPs at 25° C. In some embodiments, the viscosity may be $100 \times 10^3$ to $300 \times 10^3$ cPs at 25° C. The variation in viscosity may be due to specific applications where a more runny composition is preferred while other applications may require a more viscous composition. By way of example, the composition may easily be made with a lower and higher viscosity as well without departing from the scope of the invention. For example, another gel product, Solosite™ has a viscosity of $45$-$90 \times 10^3$ cPs at 25° C.

As noted above, the composition includes at least one topical carrier or vehicle. A wide variety of carriers or vehicles may be used. In some embodiments the at least one carrier or vehicle may have a melting point of about 37° C. or greater. Preferred carriers or vehicles understood by the applicant to be useful may include those selected from the group consisting of: a fatty ester, synthetic wax, beeswax, vegetal wax, mineral wax, a spermaceti wax constituent, carnauba wax and jojoba liquid wax. In a specific embodiment, the topical carrier or vehicle is myristyl myristate.

Myristyl myristate is a natural vegetable derived ester compound with emulsifier and opacifier characteristics. Myristyl myristate is often used in skin lotions to improve the feel of the compositions as it has the effect of thickening compositions. Myristyl myristate is an ester of myristic acid, which occurs naturally in animal or vegetable fats and oils.

In some embodiments, the at least one topical carrier or vehicle comprises from about 10% to about 30% wt of the composition. More specifically, the at least one topical carrier or vehicle comprises about 15% wt of the composition.

The interaction of honey and the other compounds of the composition is understood to be very important to achieve the desired characteristics. Honey naturally includes water (up to 18% wt). Therefore, in order to combine and stabilise a myristyl myristate and honey emulsion, a surfactant/emulsifier is required. Olive oil used in the art is an oil and is not soluble in water. Due to these properties, olive oil will only mix with melted myristyl myristate, but not the honey. In the absence of a surfactant, once the mixture is cool, myristyl myristate will go back to its solid phase, but will not be fully dispersed within the honey. Instead, the myristyl myristate and olive oil exist as a separate phase. As will be appreciated from the above, use of a surfactant and the type of surfactant is of importance.

The applicant has unexpectedly found that naturally derived short chain fatty alcohols with non-ionic surfactant properties provide the necessary surfactant properties to successfully combine the honey and wax and confer the properties desired. These compounds also tend to be milder on the skin and have a low toxicity. Unexpectedly, the short chain fatty alcohols confer a greatly increased level of stability over the art, well beyond that expected or currently observed. In some embodiments, the carbon chain length of the tail of the fatty alcohol may be from about 6 carbon atoms to about 10 carbon atoms long. In some embodiments, the carbon chain length tail may be 7 to 9 carbon atoms long. In some embodiments, the carbon chain length tail may be 8 carbon atoms long.

By way of example, non-limiting examples of short chain fatty alcohols that may be used may be selected from the group consisting of: caprylyl capryl glucoside, coco glucoside, lauryl glucoside, cetearyl olivate, sorbitan olivate, polyglyceryl-6 caprylate, polyglyceryl-6 laurate, polyglyceryl-10 laurate, polyglyceryl-5 oleate, polyglyceryl-5 dioleate, polyglyceryl-10 diisostearate, polyglyceryl-3 stearate, polyglyceryl-3 palmitate, polyglyceryl-3 polyricinoleate, glyceryl oleate, sodium stearoyl lactylate, glyceryl stearate citrate, and combinations thereof.

In a specific embodiment, the applicant has found that the naturally derived short chain fatty alcohol may be caprylyl capryl glucoside and derivatives thereof. This particular glucoside has been found by the applicants to confer the ideal properties to the composition including achieving the desired viscosity, the conversion from a gel to a skin on the wound when applied, the reduced stickiness of the composition, still allowing sufficient honey to be present in the composition to achieve the desired antibacterial function. Also a further advantage is that the glucoside is natural based being plant derived and has non-ionic surfactant properties. The fact that caprylyl capryl glucoside was successful was unexpected as this type of glucoside is normally used in various foaming and cleaning compositions rather than wound care compositions owing to its surfactant and foaming characteristics. In honey compositions, the surfactant properties appear to assist but foaming does not occur as in art compositions such as shampoos. In addition, use of glucoside and caprylyl capryl glucoside in particular conferred an improved stability, well beyond that found from other art compositions and beyond what might have been expected in the art based on published information about glucoside, particularly combination with honey of which there is no known art to the applicant's knowledge.

In some embodiments the composition contains from about 2% to about 10% wt naturally derived short chain fatty alcohol. More specifically, the composition contains from about 2% to about 7% wt naturally derived short chain fatty alcohol. In some embodiments, the composition contains about 4-6% wt naturally derived short chain fatty alcohol. In some embodiments, the composition may contain about 5% wt naturally derived short chain fatty alcohol.

In some embodiments, the honey used may have both peroxide and non-peroxide activity. Non-peroxide activity is often used interchangeably with the measurement of 'unique manuka factor' or UMF activity. Honey has inherent physical characteristics such as low pH and osmolarity that deter microbial growth however honeys with non-peroxide activity are often desired or preferred in medical applications due to the enhanced anti-microbial effects observed from such honeys including those honeys derived from the species *Leptaspermum* and specifically either *Lepiospermam scoparium* manuka honey and/or *Leptospermum polygalifolium* or jellybush honey.

In some embodiments, the composition may constitute approximately 70-90% wt honey. As should be appreciated, this is ample honey and ensures activity well beyond that of more dilute formulations with less than 50% wt such as those taught in the art.

Also as noted in the definition above, although the term 'honey' has been used, a honey derivative or honey analogue may equally be used without departing from the scope of the invention.

The sterilisation effective dose as noted above may be greater than 10 kGy. In some embodiments the dose may be greater than 20 kGy. In some embodiments, the dose may be greater than 30 kGy. In some embodiments, the dose may be 32.5 kGy to 60 kGy. The applicant has found that irradiation of the composition does not appreciably alter the stability and physical characteristics of the composition unlike some art compositions that become unstable and separate post irradiation treatment. Irradiation is important in many applications such as medical applications to ensure that there are no residual microbes that may cause infection of a wound.

The pH of the composition also remains stable during storage. In some embodiments the pH of the composition post manufacture and during storage may be between 3.0 and 6.0. The pH may be 3.0 to 5.0. The pH may be 4.0 to 5.0. The pH remains within the specified range for the duration of storage.

In some embodiments there is provided a gel composition consisting of:

a. 70-90% wt honey b. 2-15% wt myristyl myristate c. 2-10% wt caprylyl capryl glucoside.

In some embodiments, the composition is irradiated with a sterilisation effective dose of radiation.

In some embodiments, the composition is a gel with similar viscosity to that described above.

Further, the above embodiments have the same stability characteristics as that described above including stability for at least 8 days when stored at 40° C.

Aspects of the broadly described gel composition described above may also apply to more specific embodiments without departing from the scope of the invention.

As should be appreciated from the above description, the intended use of the gel composition described herein is as a wound gel that is ideally applied to wounds as a gel. The myristyl myristate or other wax helps to provide the gel consistency but without a surfactant, the myristyl myristate will not disperse into the emulsion, instead, if it mixes at all, it will exist in the mixture as hard globules within a matrix of liquid honey. This will fail the required outcome as, in the wound, once the honey melts due to the amount of exudate, the waxes will stick to the wound bed and will be hard to wash away. The use of a non-ionic surfactant being a short chain fatty acid and, in some embodiments being caprylyl capryl glucoside, meets the desired criteria well including conferring longevity during storage.

WORKING EXAMPLES

The gel composition of the present application is now described with reference to examples illustrating embodiments of the composition.

Example 1

A composition containing honey (manuka honey with a UMF level of 12+) (80% wt), myristyl myristate (15% wt) and caprylyl capryl glyceride (5% wt) was manufactured and added to a tube container. The tube container was then irradiated at 25 kGy following standard irradiation protocols used for medical wound dressings that contain honey.

Baseline control tests were completed and the composition appeared smooth and free of grittiness having a cream like consistency, a soft fine grain and little or no glucose crystals.

The pH of the composition was 3.5.-4.5 and an antibacterial activity >10% phenol equivalent or >10 UMF activity over the shelf life.

Example 2

A composition containing honey (jellybush honey with a UMF level of 12+) (80% wt), myristyl myristate (15% wt) and caprylyl capryl glucoside (5% wt) was manufactured and added to a tube container. The tube container was then irradiated at 25 kGy following standard irradiation protocols used for medical wound dressings that contain honey.

Baseline control tests were completed and the composition appeared smooth and free of grittiness having a cream like consistency, a soft fine grain and little or no glucose crystals.

The pH of the composition was 3.5-4.5 and an antibacterial activity >10% phenol equivalent or >10 UMF activity over the shelf life.

Example 3

Further formulation examples are illustrated in Table 1 below showing how the composition may be made using different compounds.

Example 4

In this example, the composition of Example 1 was stored at freezer temperatures (−18° C.) and at high temperature (40° C.) for 21 days and measurements of colour, odour, appearance, texture and phase separation tested at time zero and after 3 weeks. These temperatures were chosen to simulate either extreme of shipping temperature.

The results found are summarised in Table 2 below.

TABLE 2

Sample Test Results Post Storage

| Storage Conditions | Storage Time (Weeks) | Colour | Odour | Appearance/ Texture | Phase Separation |
|---|---|---|---|---|---|
| Freezer | 3 | Light tan to brown opaque colour | Honey odour | Smooth cream like consistency | No separation |
| 40° C. | 3 | Light tan to brown opaque colour | Honey odour | Smooth cream like consistency | No separation |

Example 5

In this example, the composition of Example 1 was stored at an elevated temperature 40° C. for one week and then at 30° C. for a further 5 to 8 weeks and measurements of colour, odour, appearance, texture, phase separation, pH were tested at time zero, after 6 weeks and after 9 weeks. These temperatures were chosen to simulate a shipping temperature.

TABLE 1

Example Compositions (Excludes Carriers)

| Composition Number | Honey | | | Short Chain Fatty Acid | | | | Fatty Ester, wax or wax like compound | | | | | | | |
|---|---|---|---|---|---|---|---|---|---|---|---|---|---|---|---|
| | MH | JB | AN | CCG | CG | LG | CO | FE | SW | BW | VW | MW | SW | CW | JW |
| 1 | 80 | | | 5 | | | | 15 | | | | | | | |
| 2 | | 80 | | 5 | | | | 15 | | | | 15 | | | |
| 3 | | | 80 | 5 | | | | 15 | | | | | | | |
| 4 | 50 | | | | 5 | | | | | | 45 | | | | |
| 5 | | 90 | | | 5 | | 5 | | | | | | | | |
| 6 | | 88 | | | | 2 | | | | 10 | | | | | |
| 7 | 85 | | | | | | 10 | | 5 | | | | | | |
| 8 | | | 60 | 15 | | | | | | | | | 10 | 5 | 10 |
| 9 | 75 | | | 5 | 5 | | 5 | | 5 | 5 | | | | | |

Legend:
MH: Manuka Honey
JB: Jellybush Honey
AN: Honey Analogue
CCG: caprylyl capryl glucoside,
CG: coco glucoside,
LG: lauryl glucoside.
FE: fatty ester,
SW: synthetic wax,
BW: beeswax,
VW: vegetal wax,
MW: mineral wax,
SW: a spermaceti wax constituent,
CW: carnauba wax
JW: jojoba liquid wax The results found are summarised in Table 3 below.

TABLE 3

Accelerated Stability at 40/30° C. Test Results

| Storage Time (Weeks) | Colour | Odour | Appearance/ Texture | Phase Separation | pH |
|---|---|---|---|---|---|
| 0 | Light tan to brown opaque emulsion | Honey odour | Smooth cream like consistency | No separation | 4.4 |
| 6 | Light tan to brown opaque emulsion | Honey odour | Smooth cream like consistency | No separation | 4.4 |
| 9 | Light tan to brown opaque emulsion | Honey odour | Smooth cream like consistency | No separation | 4.3 |

There was no total weight change (0.00%) after 9 weeks storage (total weight change calculated as percent weight change of container, initial compared to 9 week test weight).

Example 6

The composition described in Example 1 was tested by wound dressing clinicians and a clinical nurse with experience in the area of wound dressings and in particular honey based wound dressing gels.

Observations were collated.

All observations made were that the composition of Example 1:
1. Was easy to apply to a wound.
2. Was easy to clean from the wound and surrounding area post application.
3. Had a uniform consistency when administered to the patient post manufacture and storage.
4. No pain or adverse effects were noted except in two cases where a slight stinging was noted by the patient on application that quickly dissipated. This observation is commensurate or better than that observed with art formulations.
5. The wound to which the composition was applied healed as per prior art formulations.

The above findings showed that the new formulation not only has increased stability but still meets all other functional criteria.

Example 7

In this Example, a trial is presented where the stability at 40° C. of a composition of Example 1 is compared to a composition modelled on that described in the art, specifically U.S. Pat. No. 6,482,442 (two formulations) and U.S. Published Application No. 2010/0233283. The specific amounts and compounds used in each composition are shown in Table 4 below.

TABLE 4

Compositions Used in 40° C. Stability Trial

| | Example 1 Composition [wt %] | US '442 Composition 1 [wt %] | US '442 Composition 2 [wt %] | US '283 [wt %] |
|---|---|---|---|---|
| Honey | 80 | 80 | 80 | 80 |
| Myristyl Myristate | 15 | 5 | 18 | 15 |
| Olive Oil | — | 15 | 2 | — |
| PEG60 | — | — | — | 5 |
| Caprylyl capryl glucoside | 5 | — | — | — |

As should be apparent from Table 4, the key difference between the different compositions was the surfactant/emulsifier used. All compositions used the same type and amount of honey while the amount of myristyl myristate was varied to either extreme taught as being acceptable in the U.S. '442 specification.

The Example 1 composition was mixed, irradiated and then stored at 40° C. When the trial ended at Day 8, the Example 1 composition had identical characteristics to that at the start of the trial, remaining stable for the 8-day duration.

The composition based on U.S. '283 was mixed together and irradiated in the same manner as the composition of Example 1. Initial characteristics of the U.S. '283 composition were the same as that of the Example 1 composition at the beginning of the trial. However, within a 12 hour time period, the U.S. '283 composition separated and hence was unstable at elevated storage temperatures.

Both of the compositions based on U.S. '442 were highly unstable. Neither sample could be mixed together even before irradiation took place. In the case of the U.S. '442 Composition 1 mixture, despite vigorous mixing the oil formed a separate layer on the top of the honey and myristyl myristate. In the case of the U.S. '442 Composition 2 mixture, again despite vigorous mixing, the myristyl myristate formed a separate layer on the top of the honey and oil.

The above results confirm the need for a surfactant/emulsifier in order to have the honey and wax such as myristyl myristate combine. The results also demonstrate how use of caprylyl capryl glucoside confers considerably greater stability than that observed using other surfactants/emulsifiers such as PEG60.

Example 8

The microbial growth stability of the composition was tested to confirm that, post storage, microbial growth did not occur. As may be appreciated, particularly for medical applications, microbial growth is of significant concern and must be avoided.

A total of five separate samples were taken based on the composition described in Example 1. The samples were stored at 40° C. for 8 days. Following storage, the samples were stored aseptically and transported to a laboratory where they were analysed for microbial growth by reference to tests for:
(a) Growth on tryptone soya broth at 22.5+/−2.5° C. for 14 days; and,
(b) Growth on thioglycollate medium at 32.5+/−2.5° C. for 14 days.

None of the five samples tested had any microbial growth detected via either test illustrating that the composition of the present invention is stable with respect to microbial growth.

Example 9

A further test was completed to determine the stability of the composition for an extended time period.

A composition containing honey (manuka honey with a UMF level of 12+) (80% wt), myristyl myristate (15% wt) and caprylyl capryl glucoside (5% wt) was manufactured and added to a tube container. The tube container was then irradiated at 35 kGy following standard irradiation protocols used for medical wound dressings that contain honey.

The trial comprised of two tests, one being a comparison between samples stored at −18 C against the same sample stored at 40 C. A second trial studied the stability of the composition in an accelerated study with honey stored at 30 C.

Table 5 below shows the results of the first study while Table 6 below shows the results of the second study.

TABLE 5

High versus Low Temperature Comparison Study

| Storage time & conditions | Colour | Odour | Appearance & texture | Phase Separation |
|---|---|---|---|---|
| 1 wk −18° C. & 3 wks 40° C. | Caramel brown | Sweet honey | Smooth cream like consistency, few glucose crystals | No separation |
| 2 wk −18° C. & 3 wks 40° C. | Opaque tan colour | Honey | Smooth cream like consistency | No separation |
| 3 wks −18° C. & 3 wks 40° C. | Light tan to Brown | Honey | Smooth cream like consistency | No separation |

TABLE 6

Accelerated stability all 30 C.

| Storage time (weeks) | Colour | Odour | Appearance/ Texture | Phase Separation | Packaging integrity | pH | Activity (non-peroxide) |
|---|---|---|---|---|---|---|---|
| 0 | Light tan to brown | Honey | Smooth cream like consistency | No separation | Intact. Text legible | 4.4 | Error with testing |
| 3 | Light brown/yellow | Sharp Honey | Smooth cream like consistency | No separation | Intact. Text legible | 4.5 | 11.89 |
| 6 | Light tan to brown opaque | Honey | Smooth cream like consistency | No separation | Intact. Text legible | 4.4 | 14.25 |
| 9 | Light brown/yellow opaque | Sharp honey | Smooth cream like consistency | No separation | Intact. Text legible | 4.3 | 16.24 |
| 12 | Light brown/yellow opaque | Sharp honey | Smooth cream like consistency | No separation | Intact. Text legible | 4 | 15.52 |
| 15 | Light brown/yellow opaque | Sharp honey | Smooth cream like consistency | No separation | Intact. Text legible | 4 | 18.39 |

The above results show that the composition is stable for at least 15 weeks when stored at 30 C and illustrates minimal difference between freezer storage versus 40 C storage. The results when applied to more normal ambient conditions support a shelf life of at least 3 years.

Example 10

A test to confirm the efficacy of the composition was completed. Ordinary honey with or without non-peroxide activity is known to have an antibacterial effect. The aim of the trial was to ensure that the composition of the invention did not compromise the antibacterial efficacy of key importance in proposed wound dressing applications.

Samples produced as per Example 1 were stored at 40° C. for 48 hours, 7 days, 14 days and 28 days and at each stage tested for microbial count. The initial inoculum and a time zero count were also measured. The results found are illustrated in Table 7 below.

TABLE 7

Antibacterial Effects for the Composition [CFU = colony forming units; <=less than]

| Challenge Organism | Initial Inoculum (CFU/gram) | Recovery Counts (CFU/gram) | | | |
|---|---|---|---|---|---|
| | | Time "0" | 48 hrs | 7 days | 14 days | 28 days |
| S. aurens | $2.9 \times 10^6$ | $1.8 \times 10^5$ | <10 | <10 | — | <10 |
| P. aeruginosa | $3.4 \times 10^6$ | $1.4 \times 10^5$ | <10 | <10 | | <10 |
| C. albicans | $5.6 \times 10^6$ | $4.7 \times 10^4$ | — | — | <10 | <10 |
| A. niger | $3.6 \times 10^6$ | $4.3 \times 10^5$ | — | — | <10 | <10 |

As shown above, the composition in accordance with embodiments described herein had an immediate and catastrophic effect on microbial growth with microbes tested being killed to less than detectable levels within 48 hours. This effect is the same as that observed using honey hence it can be concluded that the composition described herein retains the antibacterial effects of honey.

Example 11

In this example the viscosity of the composition described in Example 1 was tested. Three samples of the composition were tested and averaged to establish a viscosity figure. The method used a Brookfield Viscometer with Helipath Spindle F at 1.5 rpm and 25° C.

The test identified that the viscosity was approximately 300-400×10$^3$ cPs@25° C.

Example 12

Further viscosity measurements were taken of varying formulations based on the same method as that described in Example 11 above.

Results found are illustrated below in Table 8.

TABLE 8

Viscosity Measurements

| Sample Number | Viscosity [cPs @ °25] |
|---|---|
| 1 | 254000 |
| 2 | 210000 |
| 3 | 454000 |
| 4 | 180000 |
| 5 | 423000 |
| 6 | 168000 |
| 7 | 158000 |
| 8 | 158000 |
| 9 | 189200 |

The variation shown above illustrates how the composition viscosity may be varied for differing applications.

Aspects of the gel composition described herein have been described by way of example only and it should be appreciated that modifications and additions may be made thereto without departing from the scope of the claims herein.

What is claimed is:

1. A composition for treating a patient wherein the composition consists of:
   a. 80 wt % honey;
   b. 5 wt % caprylyl capryl glucoside; and
   c. 15 wt % of myristyl myristate;
   wherein the composition has been subjected to a sterilization effective dosage of radiation and is storage stable for a time period of at least 24 hours at 40° C.

2. The composition as claimed in claim 1, wherein the composition is stable for at least 8 days when stored at 40° C.

3. The composition as claimed in claim 1, wherein the composition is stable for at least 21 days when stored at 40° C.

4. The composition as claimed in claim 1, wherein the composition is stable for at least 15 weeks when stored at 40° C.

5. The composition as claimed in claim 1, wherein the composition is a gel.

6. The composition as claimed in claim 1, wherein the composition has a viscosity of 50×10$^3$ to 600×10$^3$ cPs at 25° C.

7. The composition as claimed in claim 1, wherein the myristyl myristate has a melting point of about 37° C. or greater.

8. The composition as claimed in claim 1, wherein the honey has both peroxide and non-peroxide activity.

9. The composition as claimed in claim 1, wherein the pH is between 3.0 and 6.0 for the duration of storage.

10. The composition as claimed in claim 1, wherein the pH is between 4.0 and 5.0 for the duration of storage.

11. The composition as claimed in claim 1, wherein the sterilization effective dosage of radiation is greater than 10 kGy.

12. The composition as claimed in claim 1, wherein the sterilization effective dosage of radiation is greater than 20 kGy.

13. The composition as claimed in claim 1, wherein the sterilization effective dosage of radiation is 25 kGy.

14. The composition as claimed in claim 1, wherein the composition has an antibacterial activity>10% phenol equivalent or>10 unique manuka factor activity over the shelf life.

15. The composition as claimed in claim 1, wherein the honey is manuka honey.

16. The composition as claimed in claim 15, wherein the composition is stable for at least 8 days when stored at 40° C.

17. The composition as claimed in claim 15, wherein the composition is stable for at least 21 days when stored at 40° C.

18. The composition as claimed in claim 15, wherein the composition is stable for at least 15 weeks when stored at 40° C.

19. The composition as claimed in claim 15, wherein the composition has a viscosity of 50×10$^3$ to 600×10$^3$ cPs at 25° C.

20. The composition as claimed in claim 15, wherein the pH is between 4.0 and 5.0 for the duration of storage.

* * * * *